(12) United States Patent  
Sommer et al.

(10) Patent No.: US 9,964,511 B2
(45) Date of Patent: May 8, 2018

(54) ELECTROCHEMICAL GAS SENSOR

(71) Applicants: Sabrina Sommer, Lübeck (DE); Frank Mett, Lübeck (DE)

(72) Inventors: Sabrina Sommer, Lübeck (DE); Frank Mett, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days. days.

(21) Appl. No.: 15/119,898

(22) PCT Filed: Feb. 11, 2015

(86) PCT No.: PCT/EP2015/000292
§ 371 (c)(1),
(2) Date: Aug. 18, 2016

(87) PCT Pub. No.: WO2015/124276
PCT Pub. Date: Aug. 27, 2015

(65) Prior Publication Data
US 2017/0059509 A1  Mar. 2, 2017

(30) Foreign Application Priority Data

Feb. 21, 2014 (DE) .................. 10 2014 002 500

(51) Int. Cl.
*G01N 27/403* (2006.01)
*G01N 27/30* (2006.01)
*G01N 27/413* (2006.01)
*G01N 27/404* (2006.01)
*G01N 27/36* (2006.01)

(52) U.S. Cl.
CPC ......... *G01N 27/4045* (2013.01); *G01N 27/36* (2013.01)

(58) Field of Classification Search
CPC .... G01N 27/403; G01N 27/28; G01N 27/304; G01N 27/308; G01N 27/413
See application file for complete search history.

(56) References Cited

U.S. PATENT DOCUMENTS

| | | | |
|---|---|---|---|
| 3,305,469 | A | 2/1967 | Poulos |
| 3,824,166 | A | 7/1974 | Deibert |
| 4,025,412 | A | 5/1977 | Laconti |
| 4,662,996 | A | 5/1987 | Venkatasetty |

(Continued)

FOREIGN PATENT DOCUMENTS

| | | | |
|---|---|---|---|
| DE | 100 48 240 A1 | 4/2002 |
| DE | 10 2008 044239 A1 | 6/2010 |

(Continued)

OTHER PUBLICATIONS

JP-08327588-A, English Equivalent of the abstract, Yokomatsu et al. (Year: 1996).*

*Primary Examiner* — Susan D Leong
(74) *Attorney, Agent, or Firm* — McGlew and Tuttle, P.C.

(57) ABSTRACT

An electrochemical gas sensor (10) includes a housing (11) which has a number of electrodes (31, 32), i.e. at least one working electrode (31) and at least one counter electrode (32), in addition to a liquid electrolyte (60). At least one of the electrodes (31, 32) and/or the housing (11) are at least partially formed of an absorption agent composition. A method of detecting acid gases employs the electrochemical gas sensor (10).

20 Claims, 6 Drawing Sheets

(56) References Cited

U.S. PATENT DOCUMENTS

| | | | |
|---|---|---|---|
| 4,666,565 A | 5/1987 | Dobson | |
| 5,331,310 A | 7/1994 | Stetter et al. | |
| 5,830,337 A | 11/1998 | Xu | |
| 2009/0152130 A1* | 6/2009 | Schneider | G01N 27/419 205/781 |
| 2011/0226619 A1 | 9/2011 | Eckhardt et al. | |
| 2012/0263870 A1* | 10/2012 | Hunter | G01N 27/4074 427/125 |
| 2014/0311905 A1* | 10/2014 | Stetter | B01J 31/06 204/424 |

FOREIGN PATENT DOCUMENTS

| | | |
|---|---|---|
| DE | 10 2010 021975 A1 | 12/2011 |
| EP | 0 152 636 A1 | 8/1985 |
| GB | 2 129 562 B | 5/1984 |
| JP | H06-288974 A | 10/1994 |
| JP | 08327588 A * | 12/1996 |
| JP | 2005-083956 A | 3/2005 |
| JP | 2012510612 A | 5/2012 |
| WO | 1999/01758 A1 | 1/1999 |
| WO | 2002/031485 A1 | 4/2002 |
| WO | 2010/063626 A1 | 6/2010 |

\* cited by examiner

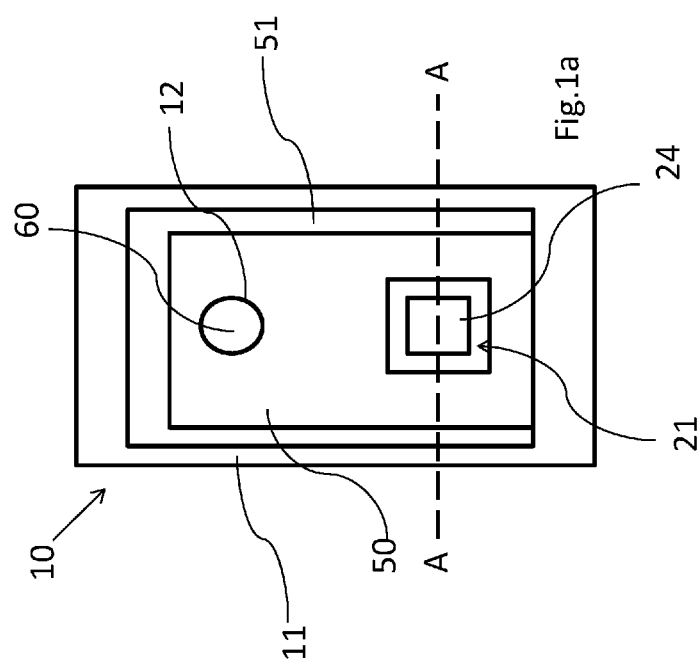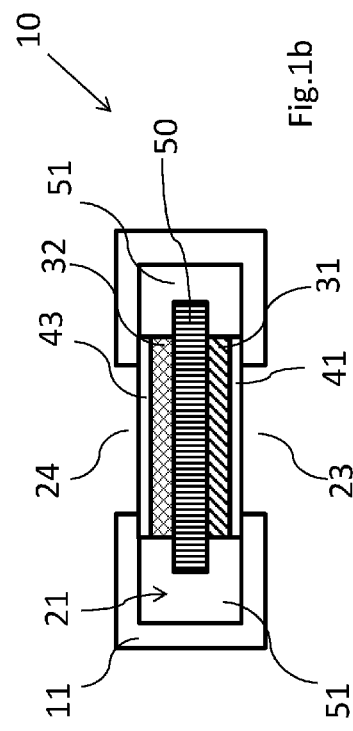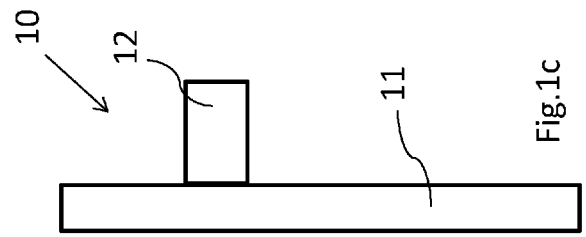

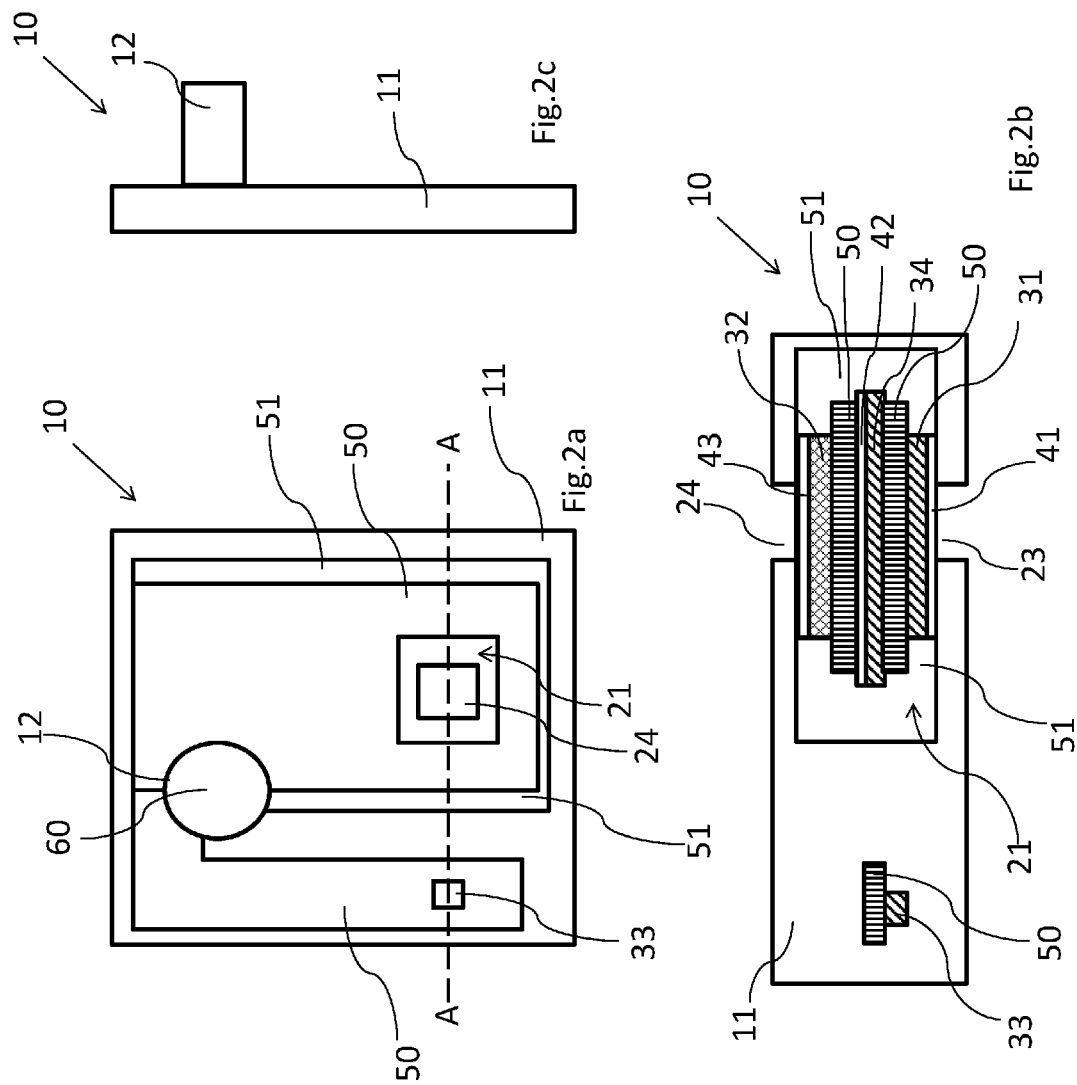

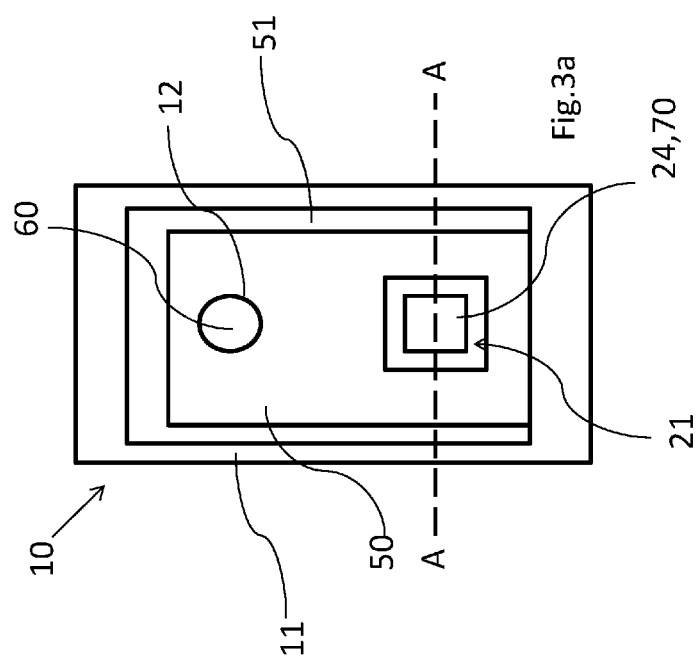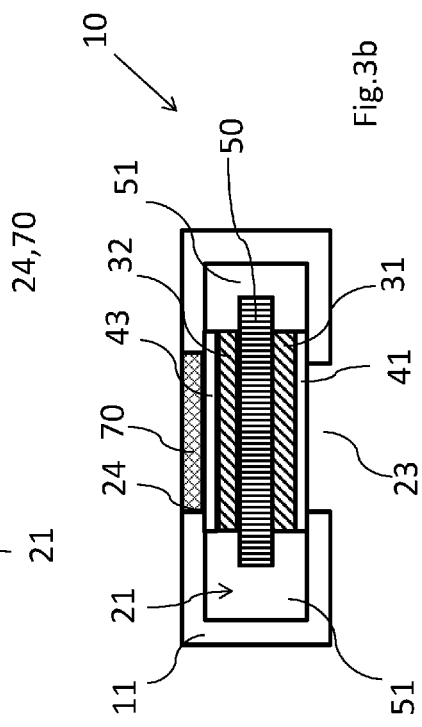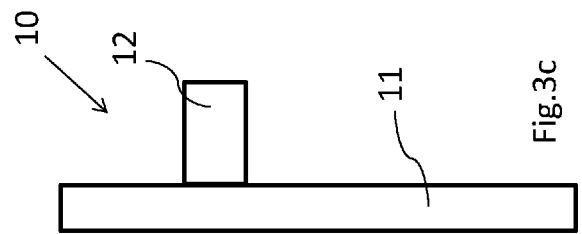

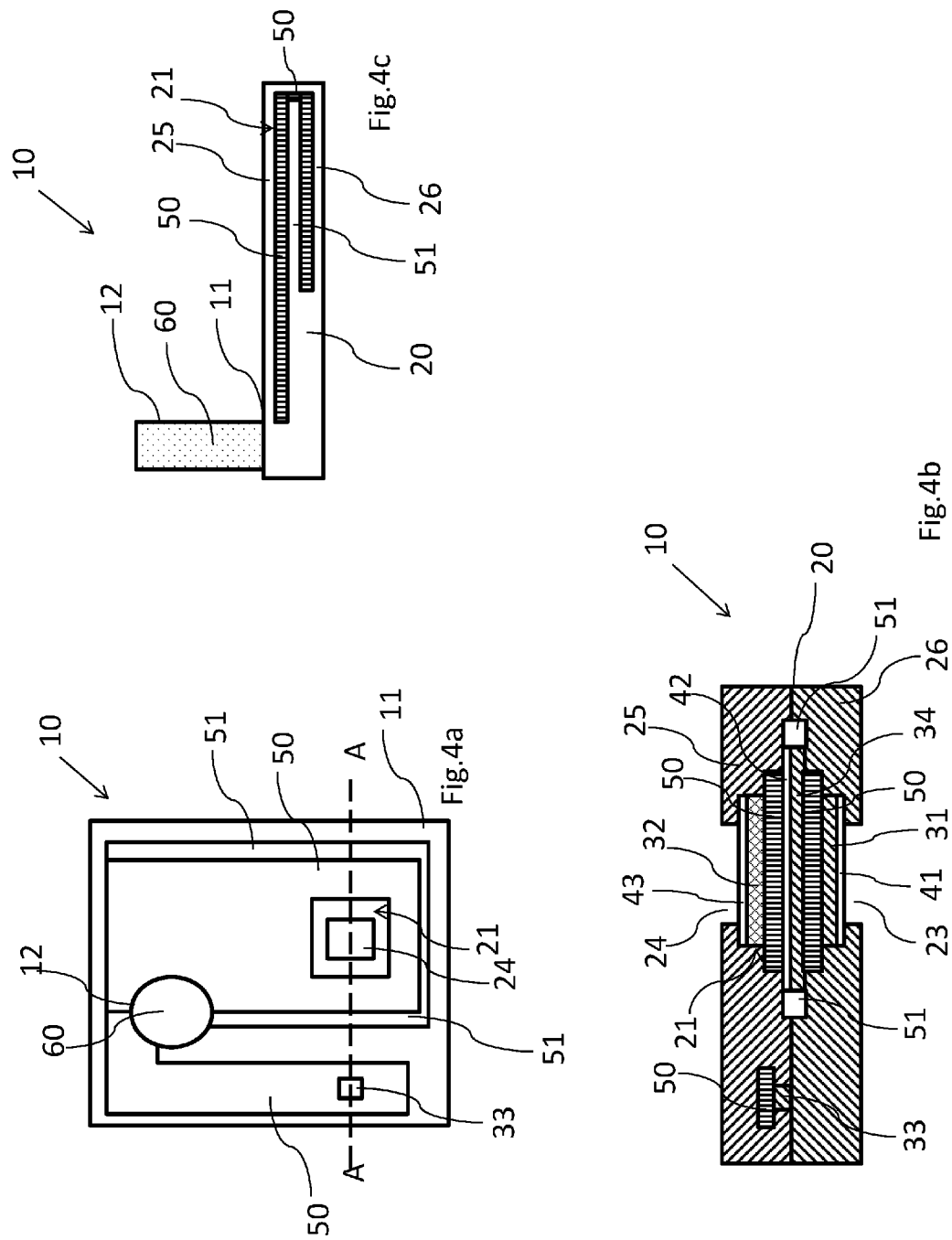

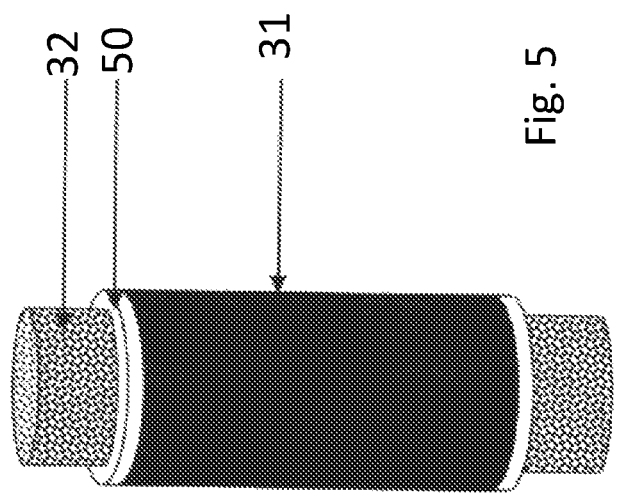

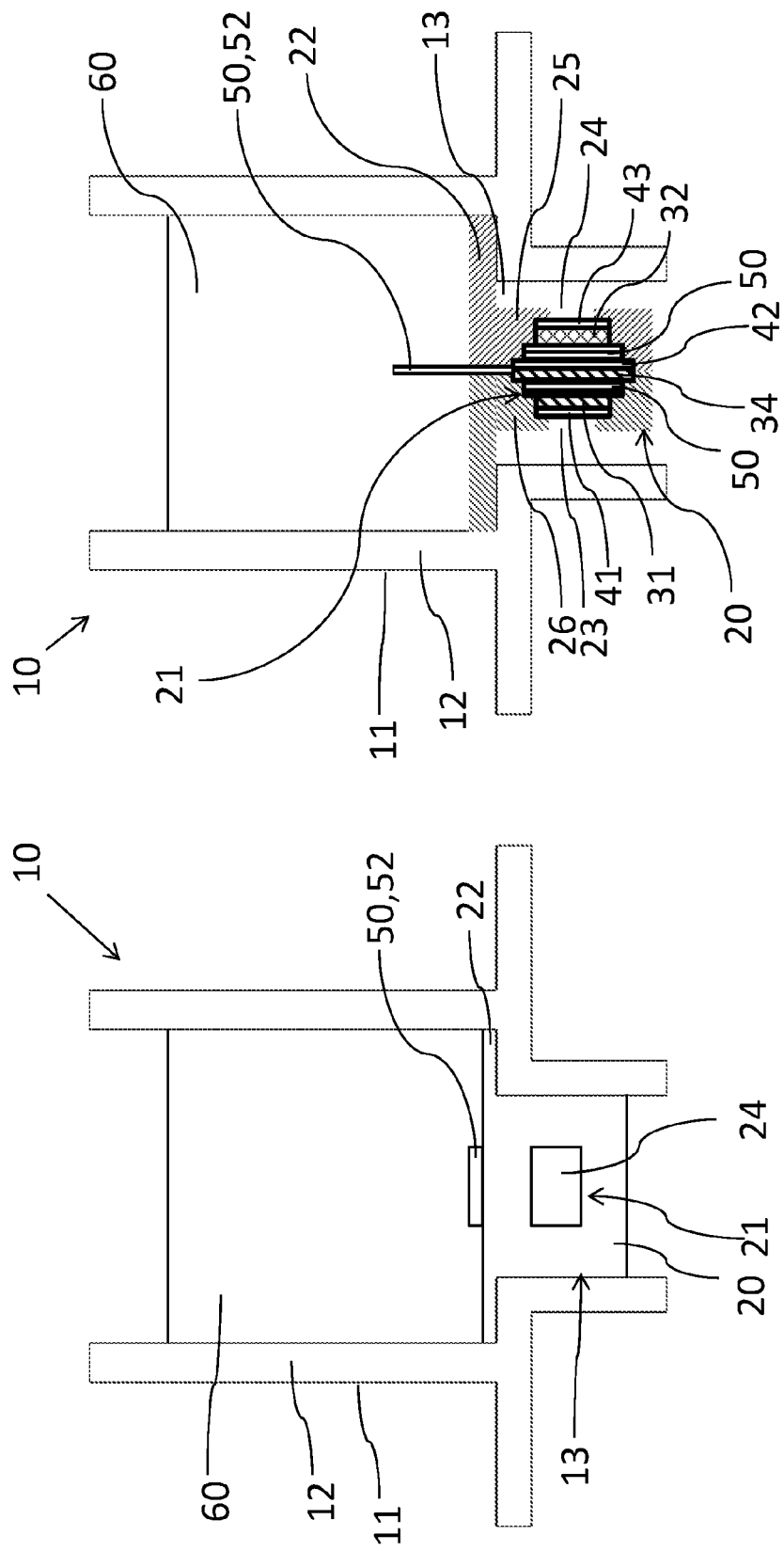

US 9,964,511 B2

ELECTROCHEMICAL GAS SENSOR

CROSS REFERENCE TO RELATED APPLICATIONS

This application is a United States National Phase Application of International Application PCT/EP2015/000292 filed Feb. 11, 2015 and claims the benefit of priority under 35 U.S.C. § 119 of German Application 10 2014 002 500.4 filed Feb. 21, 2014, the entire contents of which are incorporated herein by reference.

FIELD OF THE INVENTION

The present invention pertains to an electrochemical gas sensor with a housing, with a plurality of electrodes including, at least one working electrode and one counterelectrode as well as with a liquid electrolyte, especially to an electrochemical gas sensor that can be used to detect sour gases and/or gas mixtures containing sour gases.

BACKGROUND OF THE INVENTION

Electrochemical gas sensors are generally known. They usually have a plurality of electrodes, which are in conductive contact with an electrolyte liquid and form in this way a galvanic cell, hereinafter also called electrochemical measuring cell. There are both sensors that are used stationarily and sensors that are used in portable devices.

The industrial field of application of such sensors ranges, for example, from the chemical industry to the monitoring of refrigerating plants up to agricultural plants. The sensors are used especially to detect critical concentrations and flammable and/or toxic gases in time and to warn against a corresponding hazard. In many areas of the chemical industry, just as in the semiconductor industry, especially the detection of so-called sour gases is of great interest in this connection in order to guarantee safety at the workplace. Sour gases are generally defined in the sense of the present invention as gases that form (weak) acids, for example, halogen halides, such as HF and HCl, hydrogen sulfide or even acetic acid, when dissolved in water.

GB 2129562 B discloses in this connection the electrochemical detection of hydrogen fluoride (HF). Both the cathode and the anode of the sensor proposed there are platinum wires. A mixture of calcium bromide and calcium bromate is used as the electrolyte. However, this detection method is especially flow- and temperature-dependent.

An alternative solution is known from WO 2002/031485 A1. A measuring electrode consisting of an electrochemically active metal oxide powder is proposed here. However, such metal oxide powders may have high cross-sensitivities to other gases, as a result of which low concentrations of the target gas cannot always be detected reliably.

WO 1999/001758 A1 also discloses an electrochemical sensor, which is said to be used especially to detect hydrogen chloride. The working electrode in this sensor has an electrochemically active surface consisting of gold. However, this is dissolved over time, which may lead to the failure of the sensor in an emergency.

SUMMARY OF THE INVENTION

Based on this, an object of the present invention is to overcome these and other drawbacks of the state of the art and to provide an improved electrochemical gas sensor. In particular, a gas sensor shall be provided that has the highest possible measuring sensitivity and the best possible signal stability under permanent load. Furthermore, the gas sensor shall be able to be manufactured as cost-effectively and simply as possible.

As a solution, the present invention provides an electrochemical gas sensor comprising a housing, a plurality of electrodes, namely, at least one working electrode and one counterelectrode, as well as a liquid electrolyte, wherein at least one of the electrodes and/or the housing is comprised of an absorbent composition.

The part of the gas sensor that defines the gas sensor towards the outside is typically considered to be the housing in this connection. The housing is usually in contact with the ambient air towards the outside and forms a receptacle for the electrolyte and the electrodes inside.

An absorbent composition is defined as a composition that has at least one absorbent, the absorbent being designed such that it can react with at least one reaction product formed at the counterelectrode. An absorbent composition in the sense of the present invention may therefore consist exclusively of an absorbent in the simplest case. However, the absorbent composition preferably also contains further constituents, as they will be described in more detail below, in addition to the absorbent.

The gas to be analyzed diffuses, in principle, at first to the working electrode in such an electrochemical sensor. It is reduced there. The reaction products formed in the process migrate as ions to the counterelectrode, where they are reoxidized (reverse reaction).

Therefore, the gas to be analyzed follows in the housing a diffusion path over the course of which it first enters the electrolyte from the ambient air and at the end of which the reaction products formed at the counterelectrode flow again out of the housing. In the simplest case, the housing has at least one opening for the gas exchange with the surrounding area and an electrolyte-filled reaction chamber, in which the electrodes are located. The diffusion path of the gas to be analyzed then passes, for example, through the opening into the reaction chamber. The gas to be analyzed, dissolved in the electrolyte, flows in the reaction chamber to the working electrode, at which the direct reaction takes place. At the same time, gas formed at the counterelectrode during the reverse reaction, which is likewise dissolved in the electrolyte, flows back to the opening and from there out of the sensor. It is also conceivable that the housing has a gas inlet and a gas outlet, in which case the diffusion path leads from the gas inlet to the working electrode and from the counterelectrode to the gas outlet.

If an absorbent is provided, gas that is formed during the reverse reaction can be absorbed. It is possible in this manner to prevent this gas both from collecting at the counterelectrode and from being released to the surrounding area.

The absorbent composition may absorb especially reaction products that are formed during the reaction taking place at the counterelectrode. It is possible in this way to prevent, for example, signal breakdowns, which could otherwise develop due to an increase in the concentration of these reaction products at the counterelectrode. The absorbent composition is arranged in the gas sensor such that reaction products formed at the counterelectrode come into contact with the absorbent composition when they are moving along the above-described diffusion path in the gas sensor.

It is conceivable, for example, that one of the electrodes consists of the absorbent composition. It is also conceivable that one of the electrodes has one or more sections, which consists/consist of the absorbent composition. In other words, it is conceivable that at least one of the electrodes has an absorbent composition.

It is especially favorable if the absorbent composition is arranged at or in the counterelectrode. It is conceivable in this connection, for example, that the counterelectrode consists of the absorbent composition. The reaction products formed at the counterelectrode can be directly trapped at the counterelectrode in this manner.

It is conceivable, for example, that fluoride is formed at first during the direct reaction at the working electrode, and this fluoride will react at the counterelectrode to form HF. However, the release of HF from the gas sensor is not desirable, as a rule, because HF is highly toxic and corrosive. In addition, the released HF may lead to the above-described sensor drift when it collects in the sensor. It is therefore advantageous if the HF formed at the counterelectrode can react with the absorbent contained in the absorbent composition of the counterelectrode. It is conceivable, for example, that the HF is converted into a precipitated solid in this reaction.

It is also conceivable that at least one section of the housing consists of the absorbent composition. A section of the housing, which section is in contact with the electrolyte, is preferably formed from the absorbent composition. For example, HF formed at the counterelectrode or even another reaction product can be trapped in this manner from the electrolyte before it is released into the area surrounding the gas sensor. It is thus favorable, for example, if the housing has a recess, which forms a gas outlet, and the absorbent composition is arranged fully or partially in the recess.

For example, the absorbent composition may be arranged in the gas outlet in a plug-like manner. The absorbent composition may form a filter, through which the gas flowing out of the gas sensor must flow. The absorbent contained in the absorbent composition can thus react with the reaction product, so that release into the environment is effectively preventable. At the same time, the absorbent composition may form an outer limitation of the electrolyte-filled reaction chamber.

It is conceivable that either one or more of the electrodes consists/consist of the absorbent composition or that a part of the housing, for example, the gas outlet, consists of the absorbent composition. It is also conceivable that both at least one of the electrodes and a part of the housing consist of the absorbent composition. Furthermore, it is conceivable that one or more of the electrodes consists/consist of a first absorbent composition, while a part of the housing consists of a second absorbent composition.

It is favorable if the absorbent composition contains at least one absorbent, a carrier material and an additive. The absorbent is preferably a substance or substance mixture that can react with at least one reaction product formed at the counterelectrode. The selection of the particular concrete composition may depend, on the one hand, on which reaction products are to be expected at the counterelectrode, and, on the other hand, on whether the absorbent composition shall be used as an electrode material and/or as a component of the housing, for example, as a filter in the gas outlet. In any case, the absorbent composition may be a composite consisting of absorbent, carrier material and additive.

If the absorbent composition is used as an electrode material, it preferably contains both material that will hereinafter be called active electrode material and material that will hereinafter be called passive electrode material. An active electrode material is defined here as a material that is electrochemically active and participates in the electro-chemical reaction of the gas sensor, which takes place at the corresponding electrode. A passive electrode material is defined as a material that does not participate in the electrochemical reaction in the strict sense of the word. The electrochemical reaction in the strict sense of the word is defined as the reaction taking place between the gas to be analyzed and the working electrode or the reverse reaction taking place at the counterelectrode. For example, the additive of the absorbent composition may be an active electrode material. It is conceivable, for example, that the active electrode material consists of carbon. However, it is also possible, of course, to use other materials, for example, metal, preferably noble metals, for example, platinum, iridium or gold, as the active electrode material. Provisions are made in a preferred embodiment for the absorbent composition to have carbon nanotubes as the additive. The carbon nanotubes are used as active electrode material and ensure the electrical conductivity as well the reactivity of the electrode.

The carrier material and/or the absorbent may be passive electrode materials.

It is, in addition, favorable, especially if the absorbent composition shall be used as the electrode material, if the absorbent composition contains an absorbent that is poorly soluble or insoluble in the electrolyte. It is preferred in this connection if the absorbent is poorly soluble or especially preferably insoluble in the electrolyte. The absorbent composition and therefore the electrode material can be prevented in this manner from gradually dissolving. By contrast, there should be a minimum solubility for the reaction product formed, so that the reaction product is not entirely insoluble but is preferably soluble only poorly. The electrode surface can renew in this way continuously to a low extent due to dissolution of the reaction product. The slow but steady dissolution of the absorbent taking place in this process takes place so slowly and over such a long period of time that the consumption of the electrode material is ideally irrelevant in relation to the overall service life of the gas sensor. At the same time, the slow but steady surface renewal makes it possible to prevent clogging of the electrode surface with reaction products.

It is favorable, furthermore, if the absorbent composition contains a carbonate compound, preferably an alkali carbonate compound or an alkaline earth carbonate compound, especially preferably $BaCO_3$, as the absorbent. This is advantageous above all if the gases to be detected are sour gases, as defined above. For example, HF formed at the counterelectrode can react with $BaCO_3$ into $BaF_2$ and $H_2CO_3$ corresponding to the following reaction equation. The $BaF_2$ formed precipitates in this case as a solid:

$$2HF + BaCO_3 \rightarrow BaF_2\downarrow + H_2CO_3$$

Even though the precipitated $BaF_2$ is deposited on or in the counterelectrode, it does so without poisoning the counterelectrode (i.e., without clogging the surface of the electrode and thus without sealing it for further reactions).

It is also favorable in this connection if the absorbent composition contains as the carrier material a fibrous material, preferably a microfibrous material, especially preferably glass fibers, microfibers and/or nanofibers, preferably polymer microfibers and/or polymer nanofibers. The absorbent contained in the absorbent composition can be applied on this carrier material. It is conceivable, for example, that the carrier material is coated with the absorbent. It is, however, especially favorable if the absorbent composition is a mixture of comminuted carrier material and powdered absorbent as well as the additive. This mixture may be prepared first, for example, as a pulpy mass similar to a pulp and then brought to the desired form, for example, as an electrode, filter or plug for the gas outlet. The carrier material ensures that the mixture of the absorbent and the particular additive can form an effective composite, on the one hand, and is, on the other hand, sufficiently moldable to be brought to the desired shape. In a first embodiment, the carrier material may be glass fiber material. It is also conceivable that they are nanofibers or microfibers or a composite of nanofibers and microfibers made of a polymer or a polymer mixture, for example, electrospun or melt-spun nanofibers, nanofiber nonwovens, microfibers or microfiber nonwovens or even comminuted composite nonwovens from nanofibers and microfibers.

If, however, the absorbent composition shall be used exclusively as a material in the area of the housing, it may be favorable if the absorbent composition contains polytetrafluoroethylene (PTFE) or a PTFE derivative as an additive. This additive may facilitate and thus improve the diffusion of gas through the absorbent composition. It is conceivable, for example, that the PTFE or PTFE derivative is PTFE fibers.

To detect sour gases, especially halogen halide gases, it is advantageous, furthermore, if the electrolyte is a composition that contains an organic solvent, preferably a composition that contains a quinoid system, and a conducting salt, which has an organic cation. The organic solvent may be selected, for example, from the group containing alkylene carbonate, alkylene carbonate mixture and/or butyrolactone, preferably from the group containing propylene carbonate, ethylene carbonate or a mixture of propylene carbonate and ethylene carbonate. It is especially preferred if the organic solvent is sulfolane.

The conducting salt may be, for example, an ionic liquid. The anion of the conducting salt is preferably selected from the group containing halides, carbonate, sulfonate, phosphate and/or phosphonate, preferably an anion selected from the group containing alkyl sulfonate, alkenyl sulfonate, aryl sulfonate, alkyl phosphate, alkenyl phosphate, aryl phosphate, substituted alkyl sulfonate, substituted alkenyl sulfonate, substituted aryl sulfonate, substituted alkyl phosphate, substituted alkenyl phosphate, substituted aryl phosphate, halogenated phosphate, halogenated sulfonate, halogenated alkyl sulfonate, halogenated alkenyl sulfonate, halogenated aryl sulfonate, halogenated alkyl phosphate, halogenated alkenyl phosphate, halogenated aryl phosphate, especially preferably an anion selected from the group containing fluorophosphate, alkyl fluorophosphate, aryl sulfonate, especially preferably from the group containing perfluoroalkyl fluorophosphate, and toluene sulfonate.

It is advantageous in this connection if the conducting salt contains as cations metal ions, onium ions or a mixture of metal ions and onium ions. For example, the metal ions may be selected from among alkali metal ions or alkaline earth metal ions, preferably from among Li, K and/or Na. It is favorable if the onium ions are selected from among ammonium, phosphonium, guanidium cations and heterocyclic cations, preferably selected from among alkyl ammonium and heterocyclic cations, especially preferably selected from among alkyl ammonium, imidazolium and/or substituted imidazolium ions, wherein the substituted imidazolium ions preferably have a structure corresponding to

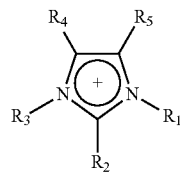

Formula II in which R1, R2, R3, R4 and R5 may be selected, independently from one another, from among —H, straight-chain or branched alkyl containing 1 to 20 C atoms, straight-chain or branched alkenyl containing 2 to 20 C atoms and one or more double bonds, straight-chained or branched alkinyl containing 2 to 20 C atoms and one or more triple bonds, saturated, partially or fully unsaturated cycloalkyl containing 3-7 C atoms, which may be substituted with alkyl groups containing 1 to 6 C atoms, saturated or fully unsaturated heteroaryl, heteroaryl-C1-C6 alkyl or aryl-C1-C6 alkyl, wherein R2, R4 and R5 are especially preferably H and R1 and R3 denote, each independently from one another, a straight-chain or branched alkyl containing 1 to 20 C atoms.

It is especially conceivable, for example, that tetrabutylammonium toluene sulfonate or 1-hexyl-3-methylimidazolium-tris(pentafluoroethyl)-trifluorophosphate is used as the conducting salt. It is thus especially advantageous if the electrolyte is a mixture of a solvent, a conducting salt and/or an organic mediator, alkylammonium toluene sulfonate and ionic liquids, with a perfluoroalkyl fluorophosphate anion.

It is favorable, furthermore, if the organic mediator is a polyhydroxy compound, which forms a quinoid system or a naphthalene system during oxidation. The organic mediator may be selected, for example, from the group containing ortho-dihydroxybenzene, para-dihydroxybenzene, substituted ortho-dihydroxybenzenes and substituted para-dihydroxybenzenes, dihydroxynaphthalene, substituted dihydroxynaphthalene, anthrahydroquinone, substituted anthrahydroquinone, preferably 1,2-dihydroxybenzene, 1,4-dihydroxybenzene, naphthohydroquinone, substituted 1,2- or 1,4-dihydroxybenzene, substituted hydroquinone, substituted naphthohydroquinone, substituted anthrahydroquinone, especially preferably substituted hydroquinone, and substituted 1,2-dihydroxybenzene. It is especially favorable in this connection if the substituents of the substituted anthraquinone, substituted 1,2-dihydroxybenzene and/or substituted 1,4-hydroquinone are selected from the group containing sulfonyl, tert.-butyl, hydroxyl, alkyl, aryl, preferably and/or tert.-butyl.

It is conceivable in another embodiment that the counterelectrode is rod-shaped. The counterelectrode may consist now at least partially of the absorbent composition. It is conceivable, furthermore, that the working electrode surrounds the rod-shaped counterelectrode in a tube-like manner. For example, the working electrode may be wound simply around the counterelectrode. It is also conceivable that the working electrode is configured as a tube and pushed over the rod-shaped counterelectrode. It is favorable in this connection if at least one separating layer, preferably a hydrophilic and/or electrolyte-impregnated separating layer, is arranged between the counterelectrode and the working electrode.

It is also conceivable in all other conceivable embodiments that one or more separating layers are arranged between the counterelectrode and the working electrode. The separating layer is preferably likewise hydrophilic and/or electrolyte-impregnated.

In any case, the separating layer may be in a fluidic connection with an electrolyte reservoir. For example, the gas sensor may be configured such that it has a reaction chamber, in which the electrodes are arranged, and an electrolyte reservoir, in which the liquid electrolyte is contained. The electrolyte can be sent in this manner to the electrodes from the electrolyte reservoir by means of the separating layer. The separating layer preferably extends over and beyond the reaction chamber to the electrolyte reservoir. It can thus have a wick effect, by which the electrolyte is transported to the electrodes. The separating layer can thus have a wick effect. In other words, it is seen that the separating layer can form an electrolyte line between the electrolyte reservoir and the electrodes. To keep the distance over which the electrolyte is transported by means of the wick effect of the separating layer as short as possible, it is conceivable that the electrolyte channels are formed laterally parallel to the electrodes covered by the separating layer.

It is also conceivable in all these exemplary embodiments that the gas sensor has, furthermore, a protective electrode. It is especially favorable in this connection if the protective electrode is arranged between the working electrode and the counterelectrode. The protective electrode can prevent, for example, gas generated at the counterelectrode from flowing back to the working electrode and from leading to incorrect signals there. It is advantageous in this connection if a diffusion-limiting separating layer is arranged between the counterelectrode and the protective electrode, e.g., in the form of a glass fiber nonwoven.

Furthermore, the gas sensor may have a reference electrode. For example, a reference electrode having a flat configuration may be arranged laterally from the working electrode and/or laterally from the counterelectrode.

All conceivable embodiments of the gas sensor according to the present invention are especially suitable for use for detecting sour gases and/or gas mixtures that contain sour gases, preferably for detecting HF, HCl and/or acetic acid. The HF and/or HCl formed at the counterelectrode can effectively be prevented from being able to be released by means of the absorbent composition. The use of a corresponding gas sensor has especially the advantage that the sensor is resistant to continuous gas exposure. Such a sensor has a good measured signal decay characteristic, i.e., the sensor will again show the zero value in a short time at the end of the measured signal. The development of drift of the measured signal during continuous gas exposure can be prevented to the greatest extent possible. Furthermore, the use of such a gas sensor according to the present invention has the advantage that no toxic and/or corrosive gases are released from the sensor.

Further features, details and specifics appear from the figures and exemplary embodiments described below. It is obvious that these exemplary embodiments are only exemplary and that further variants and exemplary embodiments will readily appear to the person skilled in the art on the basis of this specification.

The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1a is a schematic top view showing a design of a gas sensor according to the present invention, in which the counterelectrode consists of the absorbent composition;

FIG. 1b is a schematic cross sectional view through the reaction chamber of the gas sensor along line A-A in FIG. 1a;

FIG. 1c is a schematic side view of the gas sensor of FIG. 1a;

FIG. 2a is a schematic top view showing a design of a gas sensor according to the present invention with an auxiliary electrode, which consists of the absorbent composition;

FIG. 2b is a schematic cross sectional view through the reaction chamber of the gas sensor along line A-A in FIG. 2a;

FIG. 2c is a schematic side view of the gas sensor of FIG. 2a;

FIG. 3a is a schematic top view showing a design of a gas sensor according to the present invention, in which the absorbent composition forms a plug in the gas outlet of the gas sensor;

FIG. 3b is a schematic cross sectional view through the reaction chamber of the gas sensor along line A-A in FIG. 3a; and FIG. 3c is a schematic side view of the gas sensor.

FIG. 4a is a schematic top view showing a design of a gas sensor according to the present invention;

FIG. 4b is a cross sectional view through the reaction chamber of the gas sensor along line A-A in FIG. 4a; and FIG. 4c is a schematic side view of the gas sensor;

FIG. 5 is a schematic perspective view showing a design of an electrode arrangement according to the present invention, in which a separating layer and a working electrode are wound around a rod-shaped counterelectrode consisting of the absorbent composition;

FIG. 6a is a schematic sectional view showing an alternative schematic design of a gas sensor according to the present invention; and FIG. 6b is a schematic sectional view showing the sensor shown of FIG. 6a rotated by 90°.

DESCRIPTION OF THE PREFERRED EMBODIMENTS

Referring to the drawings, The gas sensor 10 shown in FIGS. 1a through 1c, 2a through 2c, 3a through 3c, 4a through 4c, 6a and 6b has a housing 11, which encloses a reaction chamber 21. A first recess 23 and a second recess 24 are formed in the housing 11. The first recess 23 is a gas inlet, through which gas to be analyzed can flow into the reaction chamber 21. The second recess 24 is a gas outlet, through which gas formed at the counterelectrode 32 can flow out of the reaction chamber 21. The electrodes 31, 32 of the gas sensor 10, namely, the working electrode 31 and the counterelectrode 32, are arranged in the reaction chamber 21. There is a separating layer 50 between the working electrode 31 and the counterelectrode 32. The separating layer 50 is hydrophilic.

Furthermore, there is a hydrophobic membrane 41 between the working electrode 31 and the first recess 23. Another hydrophobic membrane 43 is located between the counterelectrode 32 and the second recess 24. The two hydrophobic membranes 41, 43 prevent electrolyte 60 from escaping from the reaction chamber 21 and at the same time protect the electrodes 31, 32 located opposite the recesses 23, 24 from dust and contamination, which could otherwise possibly be introduced into the reaction chamber 21 through the recesses 23, 24.

The gas sensor 10 has, furthermore, an electrolyte reservoir 12, in which a liquid electrolyte 60 is contained. It is seen that the separating layer 50 connects the electrolyte reservoir 12 with the reaction chamber 21. The separating layer 50 is impregnated with the liquid electrolyte 60. The reaction chamber 21 is in fluidic connection in this way with the electrolyte reservoir 12. Electrolyte channels 51 are formed on the side of the separating layer 50. These are used to support the fluidic connection between the electrolyte reservoir 12 and the reaction chamber 21.

The gas sensor 10 shown in FIGS. 2a through 2c and 4a through 4c has, furthermore, a reference electrode 33. It is seen that the reference electrode 33 is also connected with the electrolyte reservoir 12 via the separating layer 50. As can also be seen, the reference electrode 33 is covered by the separating layer 50 in the examples shown. It is, however, also conceivable in a variant, not shown, that the reference electrode 33 is embedded in the separating layer 50. In any case, the reference electrode 33 is also in fluidic connection with the electrolyte reservoir 12, so that the electrolyte 60 is sent to the reference electrode 33 from the electrolyte reservoir 12 by means of the separating layer 50. It is seen in the top view shown in FIG. 2a that the reference electrode 33 is arranged at a laterally spaced location from the electrodes 31, 32, 34 arranged in the reaction chamber 21. However, all electrodes of the gas sensor 10 are at the same time in a conductive contact with one another through the electrolyte 60.

The gas sensor 10 shown as an example in FIGS. 2a through 2c and 4a through 4c has, in addition to the electrodes 31, 32, 33 already described, a protective electrode 34 arranged between the working electrode 31 and the counterelectrode 32. It is seen that the electrodes 31, 32, 34 are arranged in a sandwich-like manner. The separating layer 50 is arranged above the working electrode 31. It is seen that the separating layer 50 fully covers the working electrode 31. The protective electrode 34 is arranged above the separating layer 50. The protective electrode 34 is covered by a membrane 42. The membrane 42 is a diffusion-limiting membrane in a special variant. Another layer of the separating layer 50 is formed above the membrane 42. The counterelectrode 32 is arranged on this separating layer 50. The protective electrode 34 is designed in this arrangement of the electrodes 31, 32, 34 such that the surface area of the protective electrode 34 is larger than the surface area of the working electrode 31 and larger than the surface area of the counterelectrode 32.

In the embodiment shown in FIGS. 4a through 4c as well as 6a and 6b, the housing 11 is formed by an electrolyte reservoir 12 and an electrode carrier 20. The part of the housing 11 facing the viewer is shown as being transparent in the view shown in FIG. 4a especially in the area of the electrode carrier 20 to illustrate how the arrangement of the components described below may be in the interior of the electrode carrier 20.

A liquid electrolyte 60 is present in the electrolyte reservoir 12 here as well. The electrode carrier 20 has a reaction chamber 21. Gas can enter the reaction chamber 21 through a first recess 23 (can be seen in FIGS. 4b and 6b) and escape through a second recess 24. The first recess 23 is formed on the underside of the electrode carrier 20 in the example being shown, while the second recess 24 is formed in the opposite top side of the electrode carrier 20. It is obvious that it is also conceivable, as an alternative, that the first recess 23 is formed in the top side and the second recess 24 in the underside of the electrode carrier 20. It is thus seen that the electrode carrier 20 has at least one first recess 23.

The reaction chamber 21 is connected with the electrolyte reservoir 12 via a separating layer 50 here as well, so that the reaction chamber 21 is in a fluidic connection with the electrolyte reservoir 12 via the separating layer 50. To improve the feed of the electrolyte 60 even more, electrolyte channels 51 are formed on the side of the separating layer 50. It is, of course, also conceivable that only one electrolyte channel 51 is formed or that more than two electrolyte channels 51 are present.

It is seen in both FIG. 4b and FIG. 4c as well as in FIG. 6b that the reaction chamber 21 is defined by a first wall section 25 and a second wall section 26 of the electrode carrier 20. Therefore, the electrode carrier 20 forms the reaction chamber 21. The electrodes 31, 32, 34 are arranged here between the first wall section 25 and the second wall section 26. Furthermore, it is seen that the reaction chamber 21 is connected with the ambient air via the first and second recesses 23, 24. It is seen, furthermore, in FIG. 4c that the electrode carrier 20 forms a section of the housing 11 of the gas sensor 10. The housing 11 comprises here the wall of the electrolyte reservoir 12 and the wall of the electrode carrier 20. The separating layer 50 is arranged in the electrode carrier 20 such that it is in direct contact with the electrolyte 60 present in the electrolyte reservoir 12.

The separating layer 50, especially a section 52 of the separating layer 50 protruding from the electrode carrier 20, is in direct contact with the electrolyte 60 present in the electrolyte reservoir 12 in the alternative embodiment of the gas sensor 10 shown in FIGS. 6a and 6b as well. It is seen here as well that the electrode carrier 20 forms a section of the housing 11. The electrode carrier 20 has a fastening section 22. The electrode carrier 20 is fixed with this fastening section 22 in a receptacle 13 of the electrolyte reservoir 12. The electrode carrier 20 is arranged here such that the part of the electrode carrier 20 in which the reaction chamber 21 is formed forms a section of the housing 11. The electrode carrier 20 has an inner surface and an outer surface 28 in this area. The inner surface defines the reaction chamber 21. The outer surface 28 forms a section of the outer housing wall of the gas sensor 10.

In the exemplary embodiments shown in FIGS. 1a through 1c and 2a through 2c, the counterelectrode 32 consists of the absorbent composition 70. In a first variant, the absorbent composition 70 consists of a mixture of $BaCO_3$ as an absorbent, comminuted glass fibers as the carrier material and carbon nanotubes as the additive.

The absorbent composition 70 is arranged in the form of a plug in the recess 24, which forms the gas outlet, in the gas sensor 10 shown in FIGS. 3a through 3b. Gas flowing out of the gas sensor 10 must now flow through the recess 24, i.e., through the gas outlet, and therefore through the absorbent composition 70. In a first variant, the absorbent composition 70 consists of a composition that contains $BaCO_3$ as the absorbent, glass fibers as the carrier material and Teflon fibers as an additive. In a second variant, the absorbent composition 70 consists of $CaCO_3$ as an absorbent, glass fibers as a carrier material and Teflon fibers as an additive. It is also conceivable, as an alternative, that another alkali carbonate or alkaline earth carbonate is contained as the absorbent in the absorbent composition 70.

In one embodiment, not shown, the gas sensor 10 is configured as shown in FIGS. 1a through 1c. In addition to the counterelectrode 32 consisting of a first absorbent composition, absorbent composition 70 may also be arranged in this embodiment in the form of a plug in the recess 24 that forms the gas outlet. In a first variant, the absorbent composition 70 has the same composition as the first absorbent composition, of which the counterelectrode 32 consists. The absorbent composition contains here $BaCO_3$ as an absorbent, glass fibers as a carrier material and carbon nanotubes as an additive. In a second variant, the absorbent composition 70 has a different composition than the absorbent composition of which the counterelectrode 32 consists. In this variant, the absorbent composition, of which the counterelectrode 32 consists, contains $BaCO_3$ as an absorbent, glass fibers as a carrier material and carbon nanotubes as an additive. The absorbent composition 70, which is arranged in the recess 24, i.e., in the gas outlet, contains $BaCO_3$ or, in other variants, another alkali or alkaline earth carbonate as the absorbent, glass fibers as the carrier material and Teflon fibers as the additive.

In another embodiment, not shown, the gas sensor 10 is configured corresponding to FIGS. 2a through 2c, and absorbent composition 70 is additionally arranged in the recess 24, which forms the gas outlet. The absorbent composition 70 has, in a first variant, the same composition as the absorbent composition of which the counterelectrode 32 consists. As in the variants of the embodiment shown in FIGS. 1a through 1c, the absorbent composition contains $BaCO_3$ as the absorbent, glass fibers as the carrier material and carbon nanotubes as the additive. In a second variant, the absorbent composition 70 has a different composition than the absorbent composition of which the counterelectrode 32 consists. The absorbent composition, of which the counterelectrode 32 consists, contains $BaCO_3$ as the absorbent, glass fibers as the carrier material and carbon nanotubes as the additive in this variant as well. The absorbent composition 70, which is arranged in the recess 24, i.e., in the gas outlet, contains $BaCO_3$ or, in other variants, another alkali carbonate or alkaline earth carbonate, glass fibers as the carrier material and Teflon fibers as the additive.

In yet another embodiment, not shown, the gas sensor 10 is configured corresponding to the FIGS. 3a through 3c, and absorbent composition 70 is arranged not only in the recess 24, which forms the gas outlet, but the counterelectrode 32 also consists of absorbent composition. In a first variant, the absorbent composition 70 has the same composition as the absorbent composition of which the counterelectrode 32 consists. In a second variant, the absorbent composition 70 has a different composition than the absorbent composition of which the counterelectrode 32 consists. The respective absorbent compositions may have the compositions as described above in both variants.

The counterelectrode 32 consists of the absorbent composition in the embodiments of the gas sensor 10 shown in FIGS. 4a through 4c and 6a as well as 6b as well. In a first variant, not shown, absorbent composition 70 is additionally arranged in the form of a plug in the recess 24 in this case as well. The absorbent composition 70, which is arranged in the gas outlet, i.e., in the recess 24, as the same as the absorbent composition of which the counterelectrode 32 consists. Absorbent composition 70 is also additionally arranged in the form of a plug in the recess 24, which forms the gas outlet, in a second variant, not shown. However, the composition of the absorbent composition 70 arranged in the gas outlet, i.e., in the recess 24, differs from the composition of the absorbent composition of which the counterelectrode 32 consists.

A special embodiment variant of the arrangement of the working and counterelectrodes 31, 32 is seen in FIG. 5. The counterelectrode 32 is formed here from the absorbent composition and is rod-shaped. The working electrode 31 is configured as a tube (is tubular) and is plugged onto the counterelectrode 32. The separating layer 50 is formed between the working electrode 31 and the counterelectrode 32. In an alternative embodiment, the counterelectrode 32 may also be in the form of a tube (tubular).

An example of a composition of an electrolyte, as it can be used together with the above-described exemplary embodiments, is a mixture of about 60 wt. % of propylene carbonate, about 40 wt. % of ethylene carbonate, about 0.1 mole of HMIM FAP [1-hexyl-3-methyl-imidazolium-tris (pentafluoroethyl)-trifluorophosphate] and about 0.5 mole of tert.-butyl hydroquinone. This composition is, of course, variable, and the ratio of propylene carbonate to ethylene carbonate is not limited to a ratio of 60:40 wt. % by any means. The molar quantity of HMIM FAP and tert.-butyl hydroquinone contained is also variable.

All the features and advantages, including configuration details, arrangements in space and method steps appearing from the claims, the specification and the drawings may be essential both in themselves and in the many different combinations.

While specific embodiments of the invention have been shown and described in detail to illustrate the application of the principles of the invention, it will be understood that the invention may be embodied otherwise without departing from such principles.

The invention claimed is:

1. An electrochemical gas sensor comprising:
    a housing;
    a plurality of electrodes comprising at least one working electrode and at least one counterelectrode; and
    a liquid electrolyte, wherein at least one of the plurality of electrodes or the housing, or both at least one of the electrodes and the housing is comprised of an absorbent composition, the absorbent composition comprising a carbonate compound.

2. An electrochemical gas sensor in accordance with claim 1, wherein the counterelectrode consists of the absorbent composition.

3. An electrochemical gas sensor in accordance with claim 1, wherein the housing has a recess, which forms a gas outlet, wherein the absorbent composition is arranged fully or partially in the recess.

4. An electrochemical gas sensor in accordance with claim 1, wherein the absorbent composition contains at least one absorbent, a carrier material and an additive.

5. An electrochemical gas sensor in accordance with claim 4, wherein the absorbent composition contains carbon nanotubes as the additive.

6. An electrochemical gas sensor in accordance with claim 1, wherein the absorbent composition contains an absorbent, which is poorly soluble or insoluble in the electrolyte.

7. An electrochemical gas sensor in accordance with claim 1, wherein the carbonate compound comprises an alkali carbonate compound or an alkaline earth compound, comprising $BaCO_3$ as the absorbent.

8. An electrochemical gas sensor in accordance with claim 1, wherein the absorbent composition contains a microfibrous material as a carrier material.

9. An electrochemical gas sensor in accordance with claim 1, wherein the absorbent composition contains a Teflon material as an additive.

10. An electrochemical gas sensor in accordance with claim 1, wherein the electrolyte is a composition that contains an organic solvent and a conducting salt.

11. An electrochemical gas sensor in accordance with claim 1, wherein the counterelectrode is rod-shaped.

12. An electrochemical gas sensor in accordance with claim 11, wherein the working electrode surrounds the rod-shaped counterelectrode in a tubular manner.

13. An electrochemical gas sensor in accordance with claim 1, further comprising at least one separating layer comprising a hydrophilic separating layer or an electrolyte-impregnated separating layer or both a hydrophilic and electrolyte-impregnated separating layer, is arranged between the counterelectrode and the working electrode.

14. An electrochemical gas sensor in accordance with claim 1, further comprising a protective electrode or a reference electrode or both a protective electrode and a reference electrode.

15. An electrochemical gas sensor in accordance with claim 1, wherein the absorbent composition contains a carrier material comprising glass fibers, microfibers, nanofibers, polymer microfibers or polymer nanofibers or any combination of glass fibers, microfibers, nanofibers, polymer microfibers and polymer nanofibers.

16. An electrochemical gas sensor in accordance with claim 1, wherein the electrolyte is a composition that contains an organic solvent, which contains a quinoid system, and a conducting salt, which contains an organic cation.

17. A method of detecting a gas, the method comprising the steps of:
 providing a gas sensor comprising: a housing; a plurality of electrodes comprising at least one working electrode and at least one counterelectrode; and a liquid electrolyte;
 forming at least one of the plurality of electrodes or the housing at least partially of an absorbent composition, the absorbent composition comprising a carbonate compound;
 detecting a gas with the gas sensor.

18. A method according to claim 17, wherein the step of detecting a gas with the gas sensor comprises detecting sour gases or gas mixtures containing one or more sour gas with the gas sensor.

19. A method according to claim 17, wherein HF, HCl or acetic acid or any combination of HF, HCl and acetic acid is detected with the gas sensor.

20. A method according to claim 17, wherein:
 the carbonate compound comprises an alkali carbonate compound or an alkaline earth compound comprising $BaCO_3$ as the absorbent; and
 the absorbent composition contains a carrier material comprising glass fibers, microfibers, nanofibers, polymer microfibers or polymer nanofibers or any combination of glass fibers, microfibers, nanofibers, polymer microfibers and polymer nanofibers.

* * * * *